United States Patent
Kakiuchi et al.

(10) Patent No.: US 7,628,901 B2
(45) Date of Patent: Dec. 8, 2009

(54) REFERENCE ELECTRODE, SALT BRIDGE AND IONIC CONCENTRATION MEASURING DEVICE BY THE USE OF REFERENCE ELECTRODE AND SALT BRIDGE

(75) Inventors: Takashi Kakiuchi, Kyoto (JP); Manabu Shibata, Kyoto (JP); Satoshi Nomura, Kyoto (JP); Yasukazu Iwamoto, Kyoto (JP); Mikito Yamanuki, Kyoto (JP)

(73) Assignees: Horiba, Ltd., Kyoto (JP); Kyoto University, Kyoto (JP)

( * ) Notice: Subject to any disclaimer, the term of this patent is extended or adjusted under 35 U.S.C. 154(b) by 651 days.

(21) Appl. No.: 11/432,973

(22) Filed: May 12, 2006

(65) Prior Publication Data
US 2008/0000771 A1     Jan. 3, 2008

(30) Foreign Application Priority Data
Aug. 3, 2005 (JP) .......................... P2005-224955

(51) Int. Cl.
*G01N 27/26* (2006.01)
(52) U.S. Cl. ..................... 204/435; 204/416; 204/418; 204/419; 204/420; 204/433
(58) Field of Classification Search ................. 204/435, 204/433, 416, 418, 419, 420
See application file for complete search history.

(56) References Cited

U.S. PATENT DOCUMENTS

| | | | | |
|---|---|---|---|---|
| 4,002,547 A | * | 1/1977 | Neti et al. | 204/435 |
| 4,913,793 A | * | 4/1990 | Leonard | 204/433 |
| 2004/0217017 A1 | * | 11/2004 | Kidwell | 205/792 |
| 2005/0133369 A1 | * | 6/2005 | Sovrano et al. | 204/435 |

FOREIGN PATENT DOCUMENTS

JP      11-258197      9/1999

\* cited by examiner

*Primary Examiner*—Bruce F Bell

(57) ABSTRACT

The present claimed invention is to provide a reference electrode wherein variations of a potential difference at a liquid junction can be removed almost completely, contamination of a sample solution can be minimized, a frequency to supply and replace an internal solution is lessened, the liquid junction is prevented from being clogged, high durability for a long term can be maintained and a measurement with high accuracy can be conducted, and comprises an internal electrode 21, an internal solution 22 that makes a contact with the internal electrode 21 and a liquid junction 23 that continues into the internal solution 22, wherein the liquid junction 23 is made by the use of a gelled hydrophobic ionic liquid.

20 Claims, 8 Drawing Sheets

REFERENCE ELECTRODE, SALT BRIDGE AND IONIC CONCENTRATION MEASURING DEVICE BY THE USE OF REFERENCE ELECTRODE AND SALT BRIDGE

BACKGROUND OF THE INVENTION

1. Field of the Art

This invention relates to a reference electrode to be a reference for calculating or measuring an electrode potential, a salt bridge to joint two kinds of electrolyte solutions in an electrochemical measurement cell or a chemical cell and an ionic concentration measuring device to measure an ionic concentration in a sample solution by the use of the reference electrode and the salt bridge.

2. Explanation of the Related Art

A most widely used method for measuring pH is a method using a glass electrode wherein a reactive membrane is a glass membrane, and a surface of the glass membrane generates an electric potential (difference of a potential) in accordance with pH of a sample solution when the glass electrode contacts the sample solution. In order to measure the difference of the potential, an electric potential as being a reference is required, which requires a reference electrode that can present a certain reference potential in addition to the glass electrode.

However, if a liquid junction potential generated at a time when the internal solution of the reference electrode contacts the sample solution varies, a reference potential presented by the reference electrode also varies. Then a reference electrode with an arrangement that an electrode made of Ag/AgCl or $Hg/Hg_2Cl_2$ is immersed in an internal solution comprising a KCl solution of high concentration (3.3 mol/L~saturation) and an internal solution contacts a sample solution through a liquid junction comprising a porous material such as ceramics or glass has been used commonly in order to keep the variations of a liquid junction potential between the internal solution and the sample solution to a minimum. (Japan Patent Laid open number 11-258197)

SUMMARY OF THE INVENTION

For a reference electrode having an arrangement that a highly concentrated KCl solution is used as an internal solution and the internal solution directly contacts a sample solution at a liquid junction, since a traveling speed of $K^+$ in an aqueous solution generally equals to a traveling speed of $Cl^-$ and an ionic concentration of the internal solution is overwhelmingly higher than an ionic concentration of the sample solution, the variations of the liquid junction potential between the internal solution and the sample solution can be suppressed based on a fact that $K^+$ and $Cl^-$ flow out from the internal solution to the sample solution continuously. However, with this method, it is impossible to completely eliminate the variations of the liquid junction potential due to a composition change of the sample solution and this becomes a cause of the variations of the reference potential presented by the reference electrode.

In addition, if a highly concentrated KCl solution is used as the internal solution of the reference electrode, $K^+$ and $Cl^-$ always keep moving toward the sample-solution side, resulting in the following problems.
(1) KCl flows into the sample solution, which contaminates the sample solution.
(2) The KCl concentration of the internal solution decreases because KCl flows into the sample solution, which requires refilling and replacing the internal solution.

In addition, in case that a porous plug comprising ceramics or glass is used as a permeable membrane of a liquid junction for the reference electrode having the above arrangement, there is a problem that the liquid junction is clogged, thereby to prevent an accurate measurement because AgCl migrates from the internal electrode and deposits and adheres inside the porosity of the liquid junction.

Then the present claimed invention intends to provide a reference electrode that enables to remove almost completely the variations of an electrical potential at a liquid junction, to reduce contamination of a sample solution to the minimum so as to lessen a frequency of refilling and replacing the internal solution, to avoid clogging the liquid junction and to maintain high durability for a long term so that measurement can be conducted with high accuracy.

More specifically, the reference electrode in accordance with this invention is a reference electrode comprising an internal electrode, an internal solution that makes a contact with the internal electrode and a liquid junction that is in contact with the internal solution, and is characterized by that the liquid junction is made by the use of a gelled hydrophobic ionic liquid. "The hydrophobic ionic liquid" is composed of a combination of an organic or inorganic cation and an organic or inorganic anion, means a hydrophobic salt whose melting point is less than or equal to 100° C. and whose solubility to water is less than or equal to about several mM (mmol $dm^{-3}$), and is also called as an ionic liquid or a room-temperature molten salt. In addition, "the reference electrode" is used synonymously with a reference pole, a reference (checking) electrode, a reference (standard) electrode and a comparison electrode.

The ionic liquid is a salt that is in a molten state at ambient temperature. However, if both a cation and an anion that constitute the salt are hydrophobic, the salt does not mix with water and forms an ionic liquid phase separated from the water phase. As a result, if an aqueous solution contacts the hydrophobic ionic liquid, hydrophilic ions contained in the aqueous solution can not move in the hydrophobic ionic liquid. Meanwhile the ions constituting the hydrophobic ionic liquid move (are distributed) in the aqueous solution. Since the amount of the moved ions is extremely small (the distribution coefficient is small), a distribution equilibrium is established immediately in the vicinity of the phase boundary.

The present claimed invention is achieved by focusing attention on the properties of the hydrophobic ionic liquid, and the hydrophobic ionic liquid is used as the liquid junction as a device to suppress the variation of the potential at the liquid junction between the internal solution of the reference electrode and the sample solution. For a conventional electrode wherein a highly concentrated KCl solution is used as an internal solution and a KCl solution directly contacts a sample solution, the variation of the potential at the liquid junction is suppressed because $K^+$ and $Cl^-$ make a one-way movement from the internal solution to the sample solution. On the contrary, in case that a hydrophobic ionic liquid is used as the liquid junction, an amount that the ion constituting the hydrophobic ionic liquid moves to the sample solution is extremely small.

Accordingly, since the reference electrode in accordance with this invention has this structure, it is possible to minimize contamination of the sample solution, and to eliminate the variation of the potential almost completely at the liquid junction between the internal solution of the reference electrode and the sample solution. In addition, since either the internal solution or its concentration is hardly decreased, it is possible to lessen a frequency of refilling and exchanging the internal solution. Furthermore, since the gelled hydrophobic ionic liquid is used as the liquid junction in this invention, it is possible to prevent the metal salt from depositing or adhering inside the porous plug when the metal salt elutes off from the internal electrode in case that the liquid junction comprises a permeable membrane made of a porous material and that the gelled hydrophobic ionic liquid is filled inside the permeable membrane or the gelled hydrophobic ionic liquid lies between the permeable membrane and the internal solution. In addition, it is possible to reduce a speed of elution. In this invention since the hydrophobic ionic liquid constituting the liquid junction is gelled, the liquid junction may not comprise a permeable membrane comprising a porous material.

A method for gelling the hydrophobic ionic liquid is not especially limited, and may use a high polymer compound. As the high polymer compound represented is vinylidene fluoride-hexafluoropropylene copolymer, polymethyl-methacrylate, polyacrylonitrile, polybutylacrylate, and other synthetic rubber.

In addition, as the hydrophobic ionic liquid used in this invention, the hydrophobic ionic liquid comprises a cation and an anion, wherein a cation is at least more than or equal to one of quaternary ammonium cation, quaternary phosphonium cation, or quaternary arsonium cation, and an anion is at least more than or equal to one of $[R_1SO_2NSO_2R_2]^-$ (each of $R_1, R_2$ is perfluoroalkyl group of carbon number 1 through 5 respectively), borate ion containing fluorine and tetravalent boron, bis(2-ethylhexyl)sulfosuccinate, $AlCl_4^-$, $Al_2Cl_7^-$, $NO_3^-$, $BF_4^-$, $PF_6^-$, $CH_3COO^-$, $CF_3COO^-$, $CF_3SO_3^-$, $(CF_3SO_2)_2N^-$, $(CF_3SO_2)_3C^-$, $AsF_6^-$, $SbF_6^-$, $F(HF)_n^-$, $CF_3CF_2CF_2SO_3^-$, $(CF_3CF_2SO_2)_2N^-$, or $CF_3CF_2CF_2COO^-$, and the hydrophobic ionic liquid can be properly selected from the above-mentioned combinations.

A concrete example of the cation is preferably at least more than or equal to one of a chemical formula

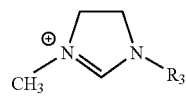

where $R_3$ expresses an alkyl group of a carbon number 1 through 12 and the alkyl group may include a heteroatom, a chemical formula

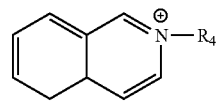

where $R_4$ expresses an alkyl group of a carbon number 12 through 18 and the alkyl group may include a heteroatom, a chemical formula

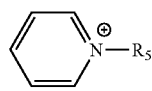

where $R_5$ expresses an alkyl group of a carbon number 12 through 18 and the alkyl group may include a heteroatom, a chemical formula

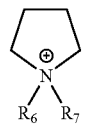

where $R_6$, $R_7$ express hydrogen or an alkyl group of a carbon number 1 through 12 and the alkyl group may include a heteroatom, or a chemical formula

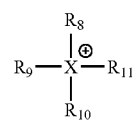

where $R_8$, $R_9$, $R_{10}$, $R_{11}$ express an alkyl group, a phenyl group or a benzyl group of a carbon number 1 through 12, and the alkyl group may include a heteroatom.

A more concrete cation is preferably at least more than or equal to one of 1-alkyl-3-methylimidazolium ion (a carbon number of the alkyl group is 4, 6, 8, 10 or 12), N-alkyl isoquinolinium (a carbon number of the alkyl group is 12, 14, 16 or 18), or N-alkyl pyridinium (a carbon number of the alkyl group is 12, 14, 16 or 18).

In addition, as a concrete example of the borate ion it is preferable that the borate ion is at least more than or equal to one of a fluoroborate ion, a tetrakis(3,5-bis(trifluoromethyl)phenyl)borate ion, or a perfluoroalkyl trifluoro borate ion (a carbon number of the alkyl group is 1 through 5).

Furthermore, if the internal solution is gelled, a volume in the support tube of the reference electrode is not easily deformable, thereby to improve a resistance to pressure. A method for gelling the internal solution may be used as the same as the method for gelling the hydrophobic ionic liquid.

The reference electrode in accordance with this invention may constitute a composite electrode in combination with an ion selective electrode such as a glass electrode.

The gelled hydrophobic ionic liquid used for the liquid junction in accordance with this invention may be used as a salt bridge for an electrochemical measurement cell or a chemical cell.

In addition, the reference electrode in accordance with this invention is characterized by comprising an internal electrode and a liquid junction that is in contact with an internal solution where the internal electrode is immersed and the liquid junction is formed by a gelled ionic liquid in a form of a membrane.

With this arrangement, since the variation of the potential at the liquid junction can be eliminated almost completely and the potassium ion or the chloride ion that the internal solution contains will not flow out into the sample solution at all, the sample solution will be scarcely contaminated, and in addition, since the internal solution neither decreases nor its concentration drops, frequency to refill and replace the internal solution can be reduced. As a result of this, the reference electrode in accordance with this invention can maintain high durability for a long term and conduct a measurement with high accuracy.

In order to make it possible to reduce the variations of difference in electric potential due to a structural change because of disturbance such as a temperature cycling and to obtain a stable liquid junction potential difference, it is preferable that the reference electrode comprises a support tube to accommodate the internal electrode and the internal solution and a membrane fixing part to fix the gelled ionic liquid membrane to a distal end face of the support tube, and the gelled ionic liquid membrane is fixed by the membrane fixing part through an elastic body lying between the distal end face of the support tube and the gelled ionic liquid membrane. The elastic body can be an O-ring.

Furthermore, the ionic concentration measuring device comprises an electrode for measurement, a reference electrode and an operational unit that calculates a concentration of an ion to be an object to measure in a sample solution based on a difference in potential generated at a time when the electrode for measurement and the reference electrode are immersed in the sample solution, and is characterized by that the liquid junction of the reference electrode is made by the use of a gelled hydrophobic ionic liquid.

In accordance with this invention, since the variation of the potential difference at the liquid junction can be eliminated almost completely and the hydrophobic ionic liquid constituting the liquid junction and the ion that the internal solution contains will not flow out into the sample solution, the sample solution will be scarcely contaminated, and in addition, since the internal solution neither decreases nor its concentration drops, frequency to refill and replace the internal solution can be reduced, and in addition, it is possible to prevent the permeable membrane comprising the porous material arranged at the liquid junction from being clogged due to deposition of the metal salt constituting the internal electrode. As a result of this, the reference electrode in accordance with this invention can maintain high durability for a long term and conduct a measurement with high accuracy.

DETAILED DESCRIPTION OF THE PREFERRED EMBODIMENTS

First Embodiment

A reference electrode in accordance with a first embodiment of the present claimed invention will be described by reference to the accompanying drawings.

Figure 1:
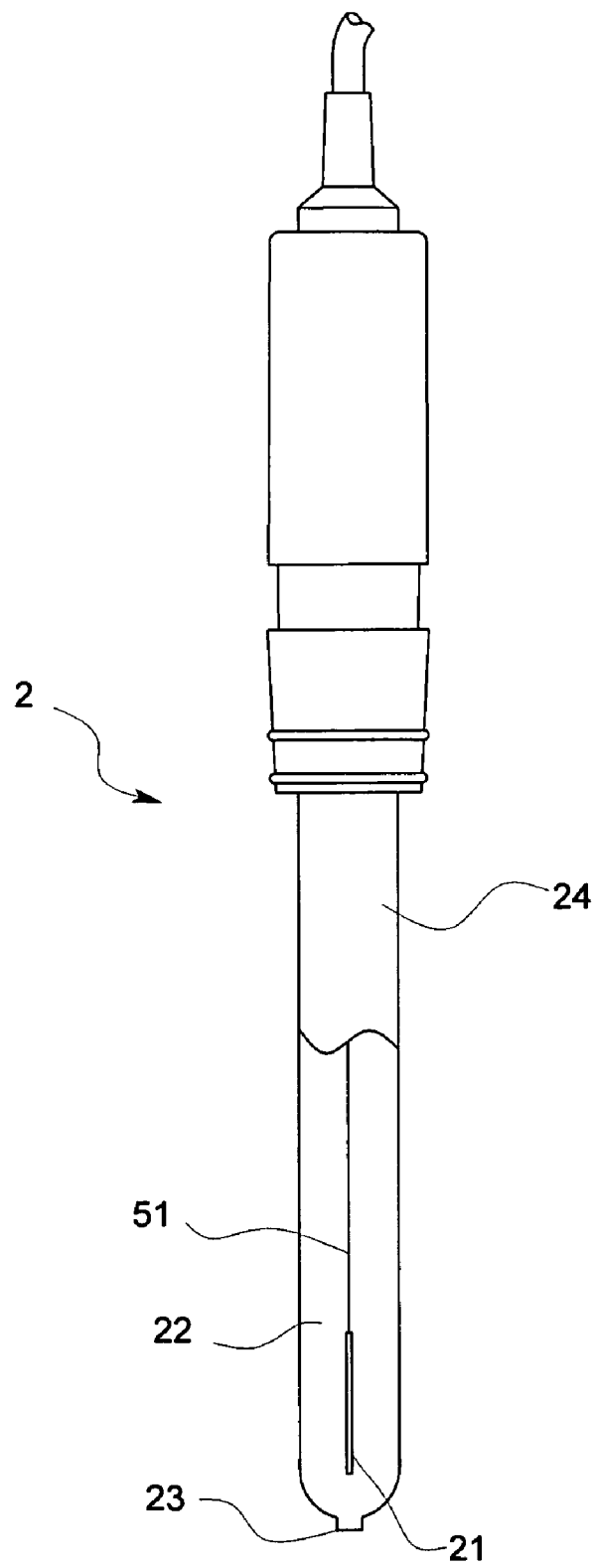
FIG. 1 is a partially broken-out sectional view showing a part of an internal structure of a reference electrode in accordance with a first embodiment of the present claimed invention.

The reference electrode 2 in accordance with this embodiment comprises, as shown in FIG. 1, a cylindrical support tube 24 made of glass and a liquid junction 23 that is connected with a distal end portion of the support tube 24. In the support tube 24 an internal electrode 21 is accommodated and an internal solution 22 is filled. A lead wire 51 is connected to the internal electrode 21 and the lead wire 51 extends outside from a proximal end portion of the support tube 24 so as to be connected with a body of a pH meter, not shown in drawings.

The internal electrode 21 of the reference electrode 2 comprises, for example, Ag/AgCl, Hg/Hg$_2$Cl$_2$, Hg/Hg$_2$SO$_4$ or the like.

In case that the internal electrode 21 consists of, for example, Ag/AgCl, a solution containing Cl$^-$ can be used as the internal solution 22 and the internal solution 22 may have any composition and may comprise, for example, a KCl solution, a NaCl solution, or an electrolyte solution comprising Cl$^-$ and a cation of a hydrophobic ionic liquid.

The hydrophobic ionic liquid used in this invention can be represented by the hydrophobic ionic liquid shown in the following table 1.

TABLE 1

| Hydrophobic Ionic Liquid | |
|---|---|
| [C$_4$mim]$^+$ | [C$_1$C$_1$N]$^-$ |
| [C$_4$mim]$^+$ | [PF$_6$]$^-$ |
| [C$_6$mim]$^+$ | [PF$_6$]$^-$ |
| [C$_8$mim]$^+$ | [C$_1$C$_1$N]$^-$ |
| [C$_8$mim]$^+$ | [C$_2$C$_2$N]$^-$ |
| [C$_8$mim]$^+$ | [PF$_6$]$^-$ |
| [TPA]$^+$ | [C$_1$C$_1$N]$^-$ |
| [THA]$^+$ | [C$_1$C$_1$N]$^-$ |
| [THA]$^+$ | [C$_2$C$_2$N]$^-$ |
| [TOA]$^+$ | [C$_1$C$_1$N]$^-$ |
| [TBA]$^+$ | [BEHSS]$^-$ |
| [TPA]$^+$ | [BEHSS]$^-$ |
| [THA]$^+$ | [BEHSS]$^-$ |
| [TOA]$^+$ | [BEHSS]$^-$ |
| [C$_{18}$Iq]$^+$ | [TFPB]$^-$ |
| [TOMA]$^+$ | [TFPB]$^-$ |
| [THA]$^+$ | [RfBF$_3$]$^-$ |

The description in the table 1 is as follows.

[C$_i$mim]$^+$: 1-alkyl-3-metylimidazolium ion (i expresses a carbon number of alkyl group) [C$_i$C$_i$N]$^-$: bis(perfluoroalkylsulfonyl) imide ion (i expresses a carbon number of perfluoroalkyl group)

[PF$_6$]$^-$: hexafluorophosphate ion

[TPA]$^+$: tetrapentylammonium ion

[THA]$^+$: tetrahexylammonium ion

[TOA]$^+$: tetraoctylammonium ion

[TBA]$^+$: tetrabutylammonium ion

[BEHSS]$^-$: bis(2-ethylhexyl)sulfosuccinate ion

[TFPB]$^-$: tetrakis(3,5-bis(trifluoromethyl)phenyl) borate ion

[C$_{18}$Iq]$^+$: 18-alkylisoquinolium ion

[TOMA]$^+$: trioctylmethylammonium ion

[RfBF$_3$]$^-$: perfluoropropyl trifluoroborate ion

The liquid junction 23 is a part where the internal solution and a sample solution contact with each other and is made of a porous material such as glass or ceramics, and a gelled hydrophobic ionic liquid whose fluidity is reduced is filled in minute porosities of the porous material.

A method to gel the hydrophobic ionic liquid is not particularly limited, and may be represented by a method by the use of a compound such as vinylidene fluoride-hexafluoropropylene copolymer, polymethylmethacrylate, polyacrylonitrile, polybutylacrylate, and other synthetic rubber.

Vinylidene fluoride-hexafluoropropylene copolymer manufactured by, for example, Aldrich Corporation can be used as the above-mentioned vinylidene fluoride-hexafluoropropylene copolymer. A method to gel the hydrophobic ionic liquid by the use of vinylidene fluoride-hexafluoropropylene copolymer is not particularly limited, however, the gelled hydrophobic ionic liquid may be obtained by dissolving the hydrophobic ionic liquid into acetone, mixing it with vinylidene fluoride-hexafluoropropylene copolymer (for example, Mw=400000), inpouring it into a glass petri dish, leaving it overnight in a state of being covered with a lid, and evaporating acetone. Hardness of the gelled ionic liquid can be varied by properly selecting a ratio of the ionic liquid, copolymer and acetone or a molecular weight of the copolymer. For example, it is possible to obtain a preferable gelled ionic liquid by making a ratio of the hydrophobic ionic liquid to a sum of copolymer and acetone one per ten in volume.

If the hydrophobic ionic liquid is filled in the porosities of the porous material constituting the liquid junction 23, the hydrophobic ionic liquid is not mixed with water, then both a solvent (water) of the sample solution and a hydrophilic ion that the solvent contains are capable of moving only a little in the liquid junction 23. Meanwhile, the ion constituting the hydrophobic ionic liquid is capable of moving toward the sample solution, however, the amount of transferred ionic liquid is negligibly small.

In addition, since the gelled hydrophobic ionic liquid is filled in the porosities of the porous material constituting the liquid junction 23, there is no chance that porosities of the porous material is clogged with a metal salt constituting the internal electrode.

Accordingly, with the reference electrode 2 of the above-mentioned arrangement in accordance with this embodiment, since the variation of the potential at the liquid junction between the internal solution 22 and the sample solution can be removed almost completely and the hydrophobic ionic liquid constituting the liquid junction 23 and the ion that the internal solution 22 contains will not flow out into the sample solution, the sample solution will be scarcely contaminated, and in addition, since the internal solution 22 neither decreases nor its concentration drops, frequency to refill and replace the internal solution 22 can be reduced. In addition, the porous material forming the liquid junction 23 will not be clogged due to deposition of the metal salt constituting the internal electrode. As a result of this, in accordance with the reference electrode 2, it is possible to provide a constant reference potential stably, which makes it possible to conduct a measurement with high accuracy.

Second Embodiment

Next, an ionic concentration measuring device by the use of a reference electrode in accordance with a second embodiment of this invention will be described by reference to FIG. 2, FIG. 3 and FIG. 4.

Figure 2:
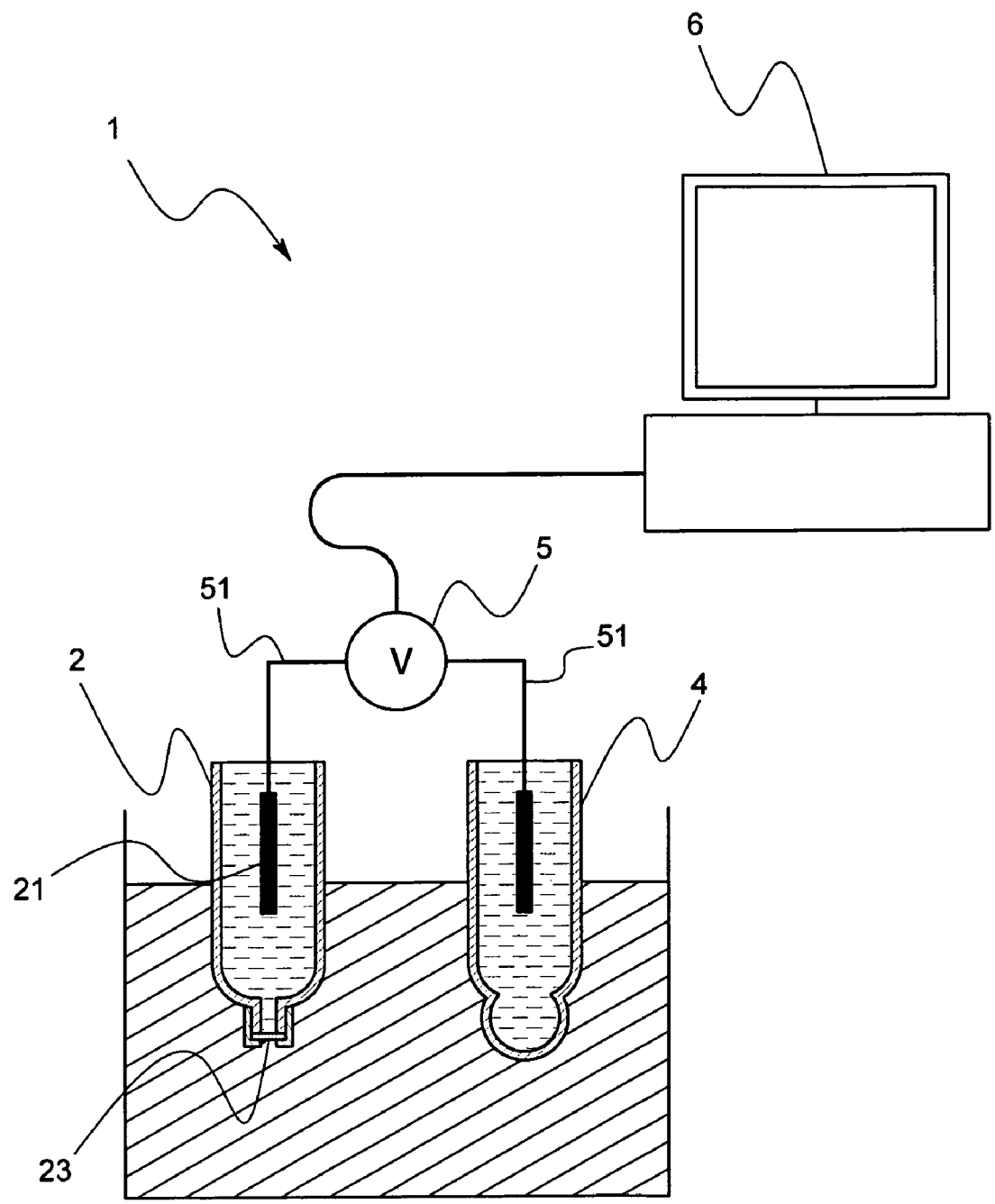
FIG. 2 is a pattern diagram of a structure of an ionic concentration measuring device in accordance with a second embodiment of the present claimed invention.

The ionic concentration measuring device 1 in accordance with this embodiment is to measure a hydrogen-ion concentration (pH) in a sample solution and comprises, as shown in FIG. 2, a reference electrode 2, an electrode for measurement 4, a potentiometer 5 that detects a potential difference generated at a time when the reference electrode 2 and the electrode for measurement 4 are immersed into the sample solution, and an operational unit 6 that calculates and displays the ionic concentration based on the potential difference detected by the potentiometer 5.

A pH electrode is used in this embodiment as the electrode for measurement 4, and an ion selective electrode may be used.

Figure 3:
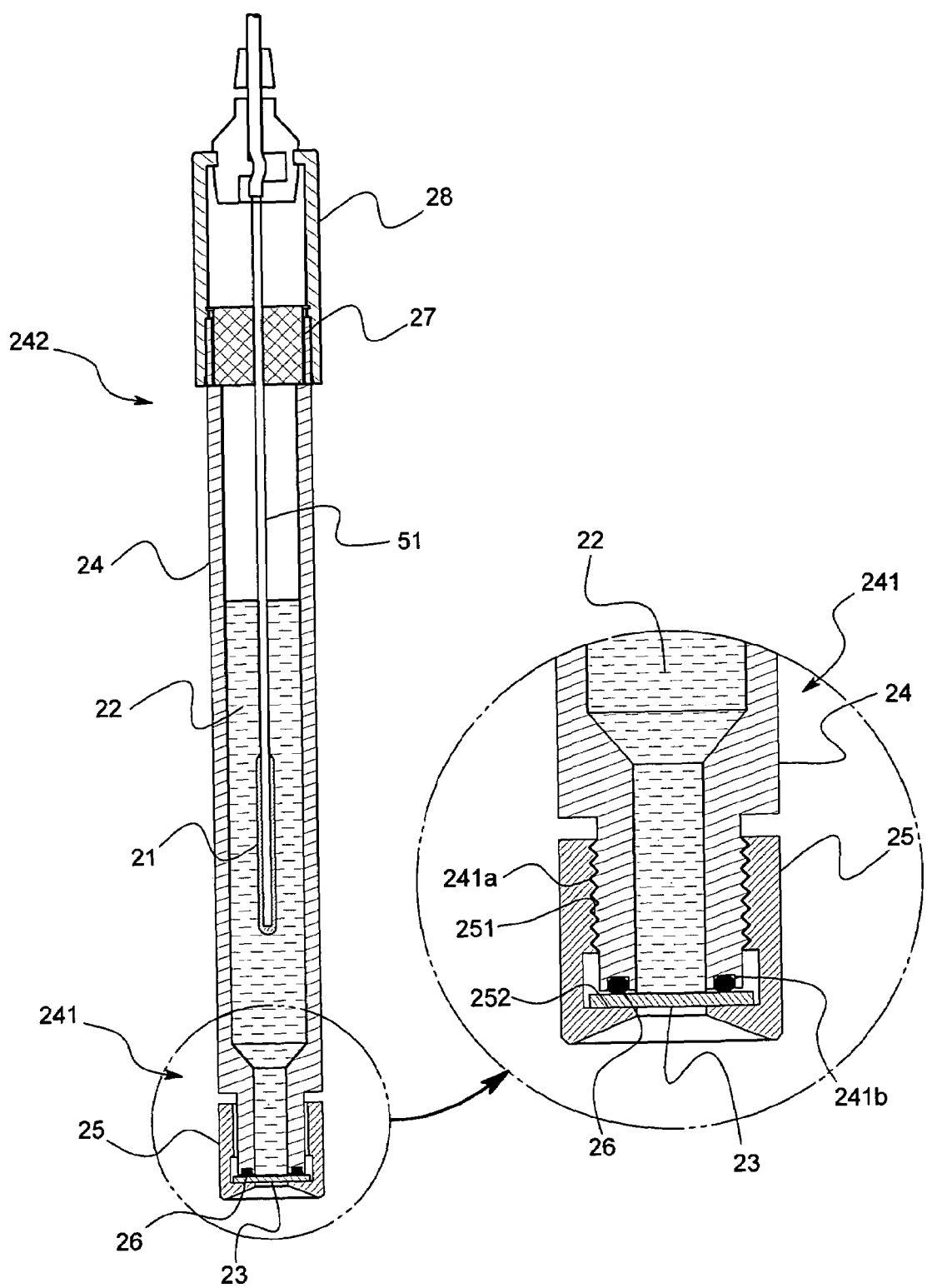
FIG. 3 is a cross-sectional view showing an internal structure of a reference electrode in accordance with this embodiment.

The reference electrode 2 comprises, as shown in FIG. 3, a cylindrical support tube 24 and a liquid junction 23 arranged at a distal end portion 241 of the support tube 24, wherein the liquid junction 23 is a gelled hydrophobic ionic liquid and the reference electrode 2 has a membrane fixing part 25 to fix the membrane 23 to the support tube 24.

The support tube 24 is to accommodate the internal electrode 21 and the internal solution 22, and its material can be a resin such as PP, PE, acrylic, PTFE (ethylene tetrafluoride), PVDF (polyvinylidene fluoride), and PEEK (polyether ether ketone), glass, metal or ceramics. In this embodiment, the support tube 24 is made of PVDF. At a proximal end portion 242 of the support tube 24 arranged are a seal packing 27 that makes a contact with the proximal end portion 242 liquidtightly and a cap 28 to cover the seal packing 27 so as not to leak the internal solution 22 from the support tube 24.

An outside diameter of a distal end portion 241 of the support tube 24 is made to be small and an external thread part 241a that is threadably mounted on the membrane fixing part 25, to be described later, is arranged on an outer circumferential surface of the distal end portion 241. In addition, a housing groove 241b to house an O-ring 26 is arranged on a distal end face of the distal end part 241 concentrically with a central axis of the support tube 24. The gelled ionic liquid membrane 23 to be the liquid junction is arranged to cover the distal end face 241a.

The internal electrode 21 is Ag/AgCl in this embodiment and a lead wire 51 is connected to the internal electrode 21. The lead wire 51 extends outside from a proximal end portion 242 of the support tube 24 through the seal packing 27 and the cap 28 and is electrically connected to the potentiometer 5. The internal solution 22 is a KCl solution and its concentration is 0.01M in this embodiment.

The liquid junction 23 is a gelled ionic liquid membrane manufactured in a shape of a membrane made of a hydrophobic ionic liquid arranged at the distal end portion 241 of the support tube 24. The membrane mentioned here is of a thickness easy to be supported by the support tube 24 with its rim portion clipped by the support tube 24, the thickness is 3 mm through 5 mm in this embodiment, and the membrane is of a disk shape with its diameter generally coinciding with a distal end face of the support tube 24. The gelled ionic liquid membrane 23 is fixed to the distal end face of the support tube 24 by the membrane fixing part 25 through the O-ring 26 as being an elastic body arranged at the distal end face of the support tube 24. The material of the O-ring may be Viton or Teflon having a chemical resistance.

A method for manufacturing the gelled ionic liquid membrane 23 is first to gel the hydrophobic ionic liquid. A method for gelling the hydrophobic ionic liquid is the same as that of the above-mentioned first embodiment. Thus manufactured membrane gel is shaped in conformity with a diameter of the electrode (an outside diameter of the distal end portion 241 of the support tube 24). In this embodiment, the gelled membrane is formed to be a shape of a membrane by the use of fluorocarbon resin such as P (VOF-HFP) (poly(vinylidene fluoride-co-hexaflouropropylene)) or PVC. In addition, as shown in FIG. 3, the hydrophobic ionic membrane 23 is made to generally coincide with or to be a little larger than the outside diameter of the distal end portion 241. In accordance with this method, the hydrophobic ionic liquid may be molded at a time of gelling the hydrophobic ionic liquid, or a membrane whose size is larger than the diameter of the electrode may be manufactured in advance and die-cut to be a necessary shape by the use of a mold.

The membrane fixing part 25 is to fix the gelled ionic liquid membrane 23 to the distal end face of the support tube 24 with a part thereof exposing outside, and is of a cylindrical shape. An internal thread part 251 that is threadably mounted on the external thread part 241a arranged on the outer circumferential face of the distal end portion 241 and a pressing face 252 that presses the gelled ionic liquid membrane 23 against the distal end face when the external thread part 241a is threadably mounted on the internal thread part 251 are arranged on the internal circumferential face of the membrane fixing part 25.

Figure 4:
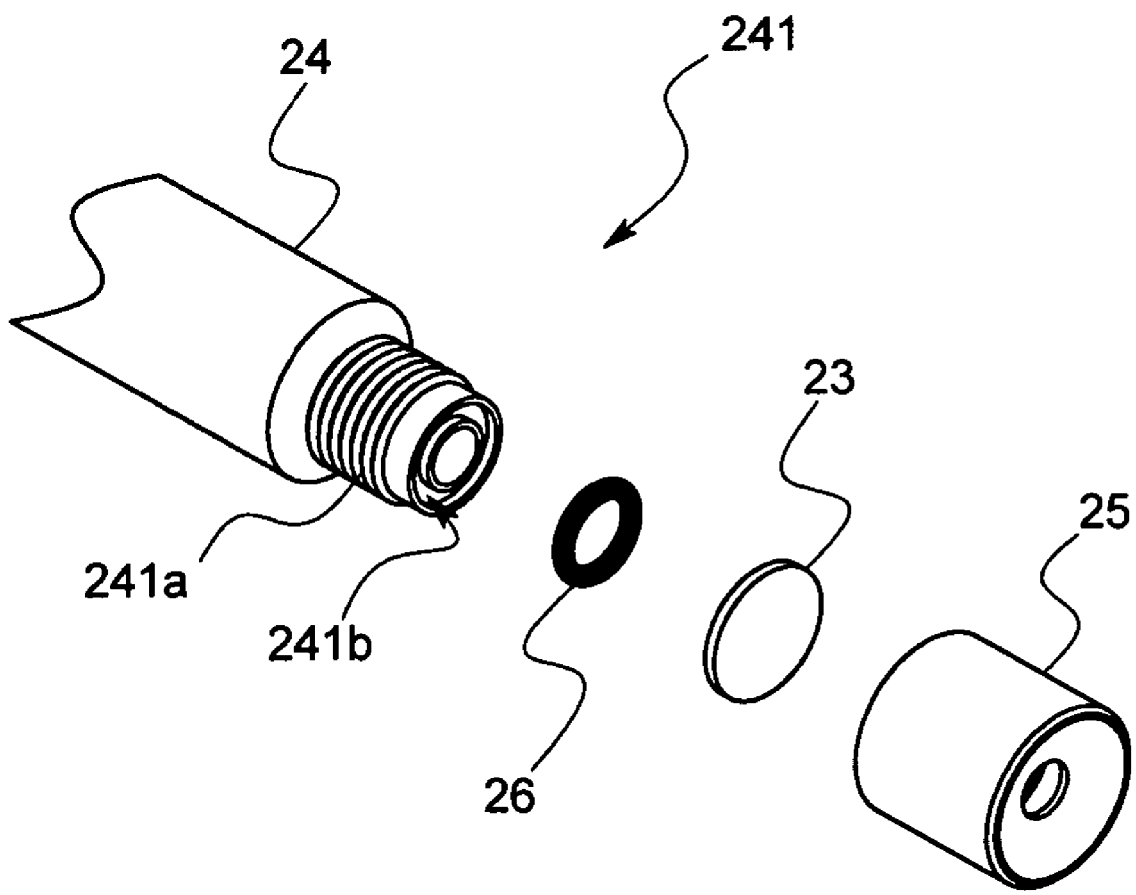
FIG. 4 is an exploded diagram of a distal end portion of the reference electrode in accordance with this embodiment.

A method for assembling is, as shown in FIG. 4, to fittingly insert the O-ring 26 into the housing groove 241b of the distal end portion 241 and then to threadably mount the internal thread part 251 arranged on the membrane fixing part 25 on the external thread part 241a arranged on the outer circumferential face of the distal end portion 241 so that the gelled ionic liquid membrane 23 is sandwiched between the distal end portion 241 and the membrane fixing part 25.

In accordance with the ionic concentration measuring device 1 of this arrangement, since the potassium ion or the chloride ion does not flow out into the sample solution at all, it is possible to minimize a change in pH or a concentration of the potassium ion or the chloride ion of the sample solution. In addition, the ionic concentration measuring device 1 can be preferably used for measuring the ionic concentration of a low ionic strength solution such as purified water or boiler water wherein a problem associated with defluxion of the internal solution 22 is especially remarkable, and in case that the sample solution is the low ionic strength solution, the change of pH can be suppressed to a point of 0.2 or under although the change of pH is about 0.5 for a conventional ionic concentration measuring device due to defluxion of the KCl solution.

In addition, it is possible to eliminate an interference influence to various ionic electrodes. With regard to, for example, a chloride ionic electrode and a potassium ionic electrode, it is possible to solve a problem of a measurement error due to the change of concentrations of $Cl^-$ and $K^+$ as being ions of measuring objects resulting from $K^+$ and $Cl^-$ flowing out into the sample solution.

With regard to a nitrate-ion-selective electrode and a sodium ionic electrode, it is possible to solve a problem that a measurement error is observed because the ions originally to be sensed is affected, and thereby the selectivity of the ionic electrode is affected.

Furthermore, in case of a thiocyanate-ion-selective electrode and a copper-ion-selective electrode, it is possible to solve a problem that a measurement error is observed due to a complex formed by a thiocyanate ion and a potassium ion and a complex formed by a copper ion and a chloride ion.

In case of a silver ionic electrode, it is possible to solve a problem that silver chloride is deposited due to a reaction with a chloride ion.

Furthermore, with regard to the reference electrode 2, a method for holding the hydrophobic ionic liquid may be conceived that the gel holding the hydrophobic ionic liquid is just arranged at the liquid junction 23 of the existing reference electrode 2. With this arrangement, the gelled membrane comes off from a component of the electrode 2 due to an influence of temperature cycling, and there is a tendency that a stable electric potential derived from the hydrophobic ionic liquid can not be obtained. With the arrangement of this embodiment, however, this problem can be preferably solved.

In addition, since the gelled ionic liquid membrane 23 is fixed to the support tube 24 through the O-ring 26, it is possible to absorb a change in the structure of the electrode due to a difference of an expansion coefficient between the component of the electrode and the hydrophobic ionic liquid membrane 23 in case that the temperature changes and to reduce a change in electrical potential. Furthermore, since the electrode 2 can be reassembled with ease, it is possible to readjust the electric potential in case that the electric potential becomes unstable. In addition, since the gelled ionic liquid membrane 23 can be replaced, it is possible to restore a performance of the electrode 2 by replacing the gelled ionic liquid membrane 23 in case that the performance is deteriorated due to contamination of the gelled ionic liquid membrane 23.

Other Modified Embodiment

The present claimed invention is not limited to the above-mentioned embodiments. The liquid junction 23 may be formed by connecting a minute cylindrical member made of glass to the distal end portion 241 of the support tube 24 made of glass and filling the gelled hydrophobic ionic liquid in the cylindrical member without using a porous material such as glass or ceramics for the liquid junction 23.

In addition, the gelled hydrophobic ionic liquid filled in the tiny cylindrical member may be sandwiched between plate shaped bodies made of a porous material such as a cellulose dialysis membrane, a millipore filter, an ion exchange membrane, glass or ceramics, or the above-mentioned membrane or the porous material may be placed only at an interface between the hydrophobic ionic liquid and the sample solution.

Furthermore, the internal solution 22 may be gelled. As a method for gelling the internal solution 22, the same method as the method for gelling the hydrophobic ionic liquid constituting the liquid junction 23 can be used. In accordance with this arrangement, resistance to pressure of the reference electrode 2 is improved since the volume of the internal solution 22, more specifically the volume of inside the support tube 24 is difficult to change.

Figure 5:
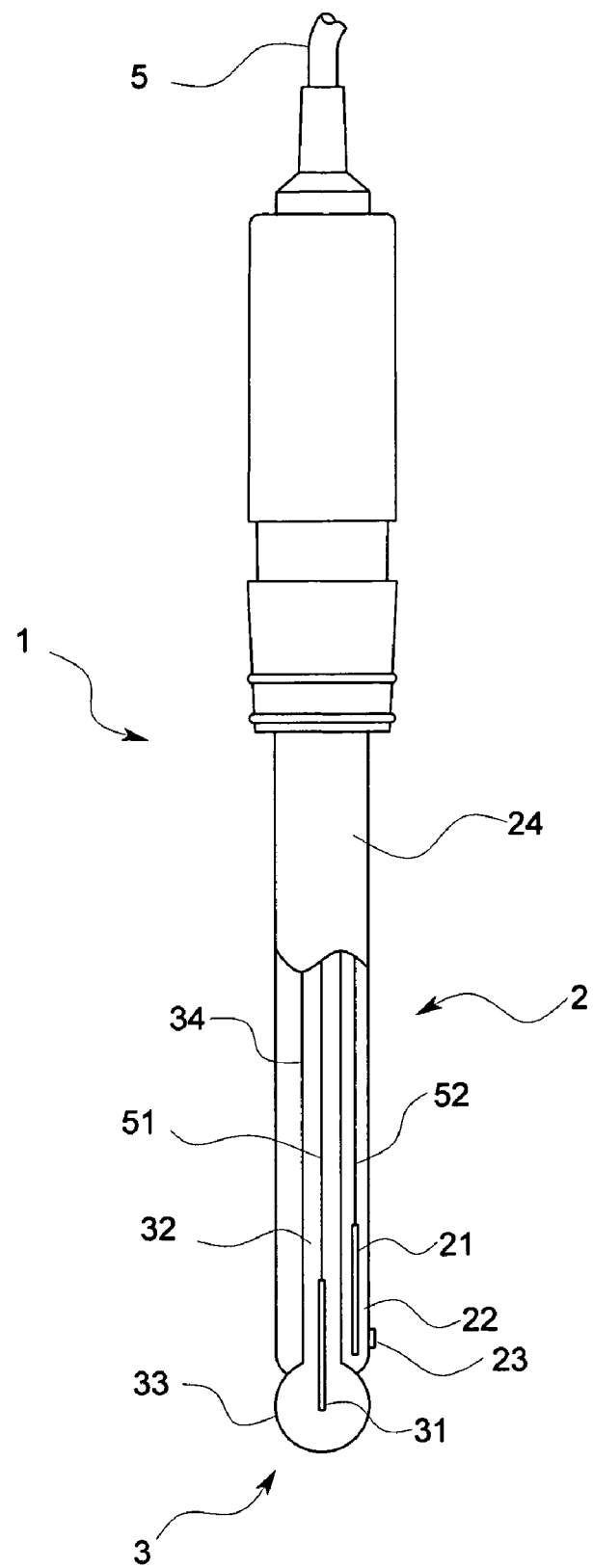
FIG. 5 is a partially broken-out sectional view showing a part of an internal structure of a reference electrode in accordance with another embodiment.
Figure 6:
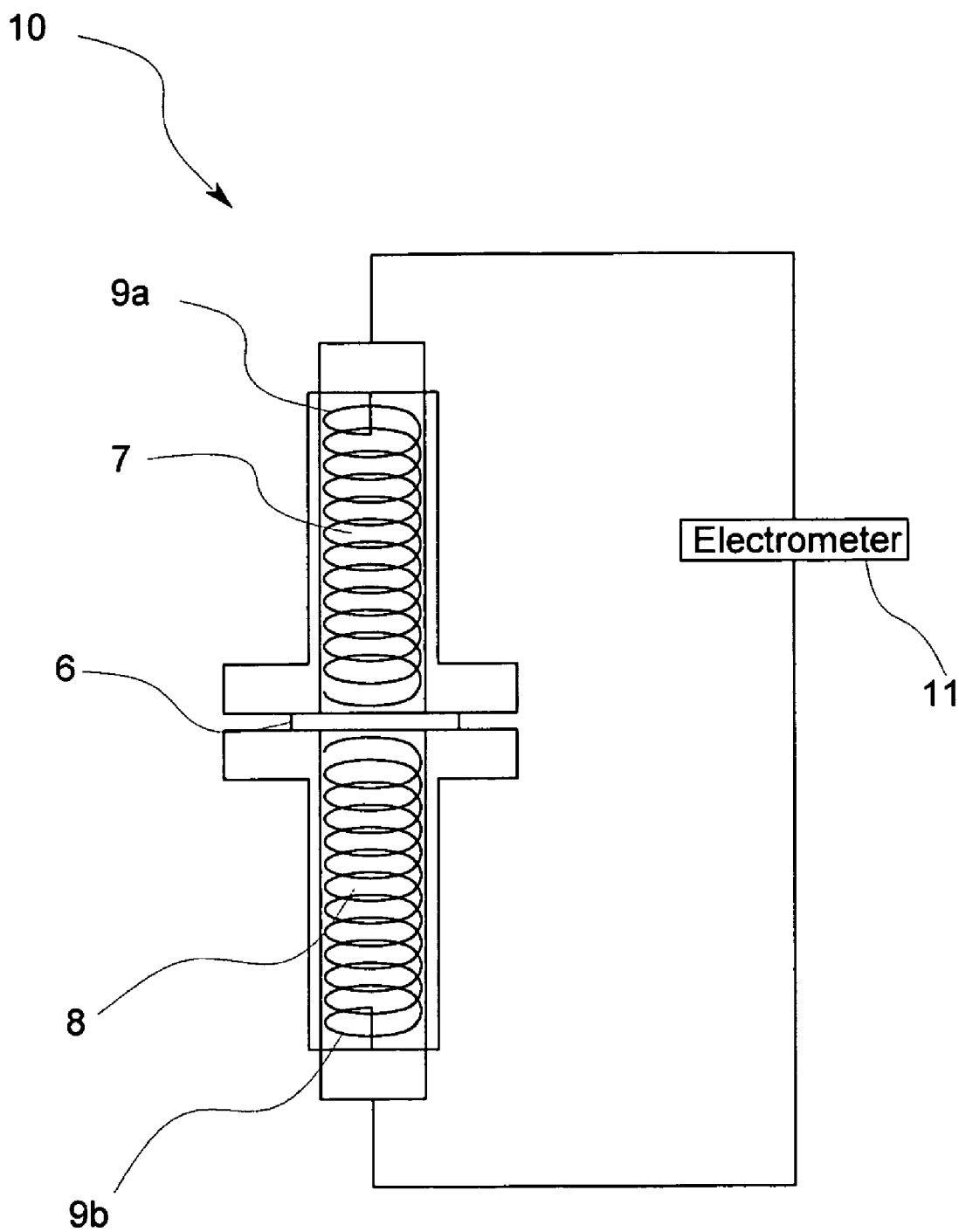
FIG. 6 is a pattern diagram showing an electrochemical cell manufactured as a model device.

As shown in FIG. 5, the reference electrode 2 in accordance with this invention may be arranged to surround a glass electrode 3 and may constitute a composite electrode 1 together with the glass electrode 3. In an embodiment shown in FIG. 5, the reference electrode 2 and the glass electrode 3 are integrally assembled in a state that the reference electrode 2 surrounds a support tube 34 of the glass electrode 3, and the glass electrode 3 comprises the cylindrical support tube 34 made of glass and a glass response membrane 33 connected with a distal end portion of the support tube 34. The glass electrode support tube 34 is made to project its distal end portion a little compared with the reference electrode support tube 24, and the glass response membrane 33 is connected to its distal end portion.

An internal electrode 31 is accommodated in the glass electrode support tube 34, and, for example, a KCl solution of pH 7 is filled as the glass electrode internal solution 32. The reference electrode 2 is arranged as the same as the above-mentioned embodiment except for the liquid junction 23 arranged at an appropriate portion of the outer circumferential wall of the reference electrode support tube 24. Lead wires 51, 52 are connected to the internal electrode 21 of the reference electrode 2 and the internal electrode 31 of the glass electrode respectively, and the lead wires 51, 52 are gathered to be a cable bundle 5 and extend outside from a proximal end portion of the support tube 2 so as to be connected to a body of a pH meter, not shown in drawings.

As mentioned above, the arrangement wherein the reference electrode 2 in accordance with this invention constitutes the composite electrode together with the glass electrode 3 makes it easier to handle the reference electrode 2.

In case that the composite electrode is constituted by the use of the reference electrode in accordance with this invention, the ion selective electrode to be combined with the reference electrode is not limited to the glass electrode, and may be a precipitation membrane electrode made of a hardly soluble polycrystal by pressure-forming, a precipitation impregnated membrane electrode wherein a matrix comprising polyvinyl chloride or silicon rubber is impregnated with a hardly soluble polycrystal, a crystal membrane electrode wherein a sensitive membrane is a single crystal such as lanthanum fluoride, or a liquid membrane electrode.

In addition, the gelled hydrophobic ionic liquid used as the liquid junction 23 in the above-mentioned embodiment may be used as a salt bridge (an agar bridge) by arranging between two kinds of electrolyte solutions for an electrochemical cell or a chemical cell.

With the arrangement wherein the gelled hydrophobic ionic liquid is used as the salt bridge, since the amount of the hydrophobic ionic liquid that flows out into the electrolyte solution is extremely small, the electrolyte solution is hardly contaminated and the hydrophobic ionic liquid is difficult to decrease, which makes it possible to reduce a frequency of filling the hydrophobic ionic liquid.

A shape of the salt bridge is not especially limited, and may be reverse-U-shaped or H-shaped according to a container to be used. In addition, a porous permeable membrane may be or may not be arranged on a liquid junction between the above-mentioned salt bridge and the electrolyte solution.

Figure 7:
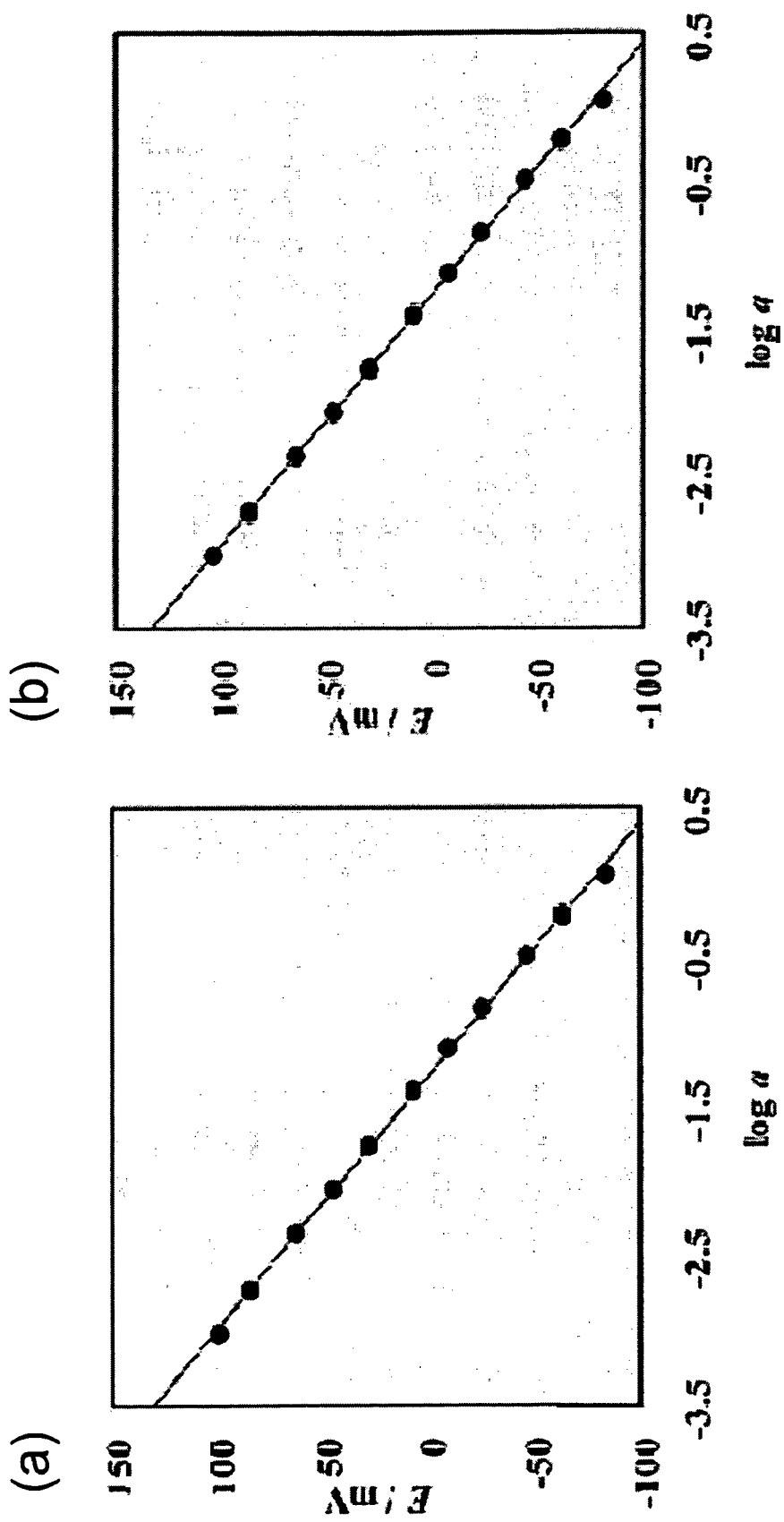
FIG. 7 is a graph showing a result of plotting a voltage between terminals recorded with changing the KCl concentration of an aqueous phase (I) to each logarithm of the average ionic activity of KCl of the aqueous phase (I).

As a model device using the gelled hydrophobic ionic liquid as the salt bridge, an electrochemical cell 10 is manufactured by sandwiching a membrane 6 of about 1 mm thickness manufactured by gelling $C_8mimC_1C_1N$ comprising a combination of a 1-octyl-3-metylimidazolium ion and a bis (perfluoromethyl-sulfonyl) imide ion with vinylidene fluoride-hexafluoropropylene copolymer between two aqueous phases (an aqueous phase (I) 7, an aqueous phase (II) 8) and inserting Ag/AgCl electrodes 9a, 9b into each aqueous phase 7, 8 respectively, and a voltage between end terminals is measured by an electrometer 11. $Cl^-$ salt of a constituent ion $C_8mim^+$ of the hydrophobic ionic liquid is dissolved in the aqueous phase (II) 8 and the composition of the aqueous phase (II) 8 is made to be constant without change. KCl comprising a hydrophilic ion is dissolved in the aqueous phase (I) 7 so that the aqueous phase (I) 7 is made to be the hydrophobic ionic liquid and an aqueous solution that does not contain a common ion. A result of plotting a voltage between the end terminals recorded with changing the KCl concentration of the aqueous phase (I) 7 to each logarithm of the average ionic activity of KCl of the aqueous phase (I) 7 is shown in FIG. 7(a). In addition, a result by the use of $C_8mimC_1C_1N$ prior to gelation is shown in FIG. 7(b).

The result shown in FIG. 7(a) showed a line with a gradient of −59.0±0.7 and the result shown in FIG. 7(b) showed a line with a gradient of −59.3±0.4 over a wide range of the concentration. The change of the voltage between the end terminals is derived from a change in electrical potential of the Ag/AgCl electrode 9a in accordance with a change in the KCl concentration, which shows that the difference of the electrical potential at the interface of the gel 6 | the aqueous phase (I) 7 does not depend on the KCl concentration. More specifically, the difference in the electrical potential at the interface of the gel 6 | the aqueous phase (I) 7 does not depend on the composition of the aqueous phase (I) 7. In addition, gelation does not exert an influence on the response of the electrical potential as evidenced by the comparison between FIG. 7(a) and FIG. 7(b).

Figure 8:
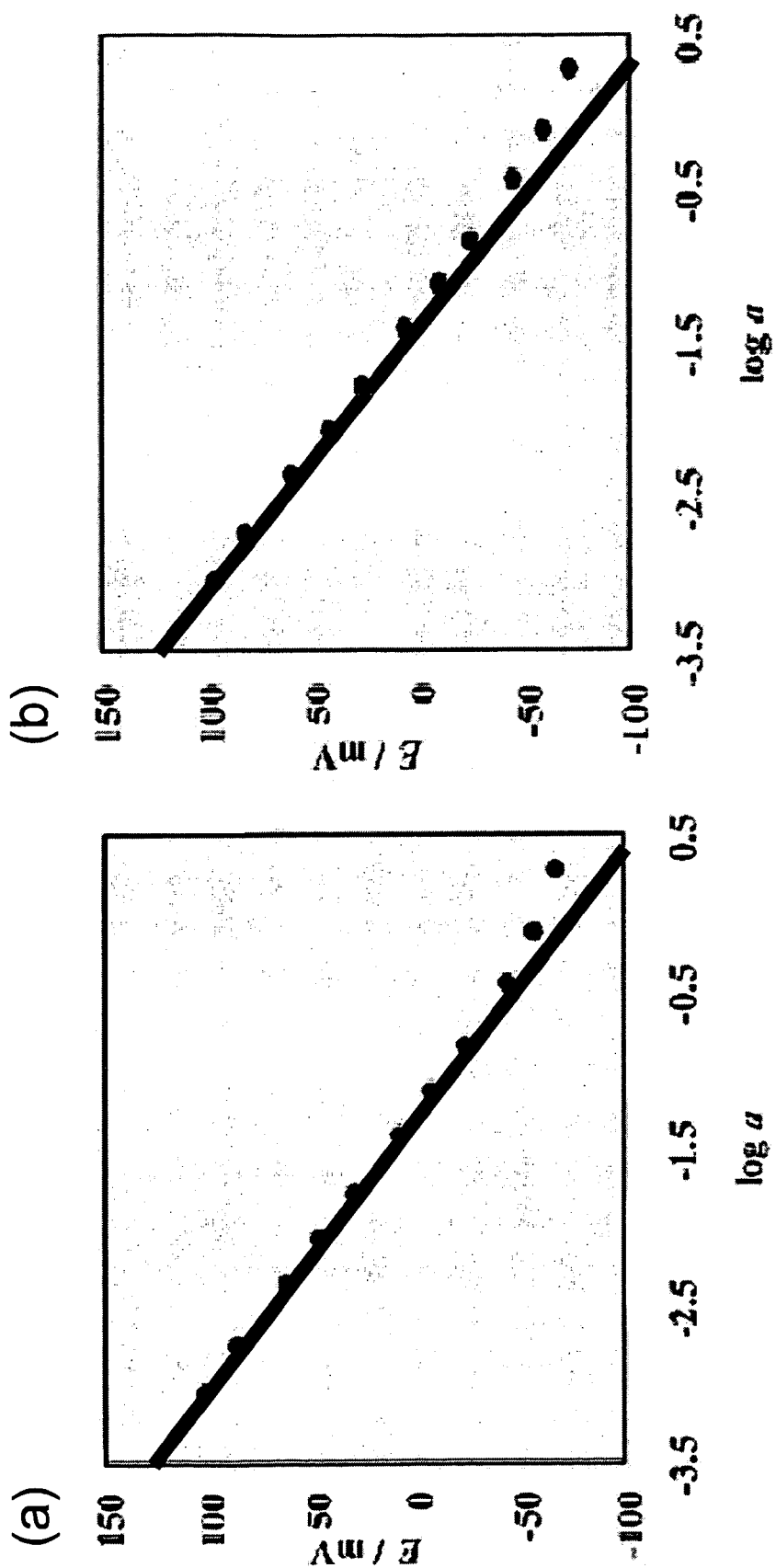
FIG. 8 is a graph showing a result of plotting a voltage between terminals recorded with changing the HCl concentration of an aqueous phase (I) to each logarithm of the average ionic activity of KCl of the aqueous phase (I).

Furthermore, results of the experiment conducted by the use of HCl instead of KCl are shown in FIG. 8(a) and FIG. 8(b). In this case, a deviance from the straight line was found at high concentrations. It shows that the deviation is slightly influenced (changed) by HCl whose liquid junction potential difference is more than or equal to 0.5 mol $dm^{-3}$. In this case also, it shows no influence on the response of the electrical potential by gelation.

A modified embodiment of the membrane fixing part in the above-mentioned second embodiment may be to fix or support the gelled ionic liquid membrane by the use of, for example, a membrane of a rough mesh to or on a distal end portion of the support tube, or to fix the gelled ionic liquid membrane by the use of a Teflon ring.

It goes without saying that there may be various modifications without departing from the spirit of the invention.

Possible Applications in Industry

The reference electrode of this invention can be preferably used without clogging the liquid junction that can be a problem at a time of measuring rain water, stream water, lake water, deionized water whose ionic strength is low. In addition, the reference electrode can be preferably used for determining industrial waste water or environmental water that requires continuous measurement.

The invention claimed is:

1. A reference electrode comprising an internal electrode, an internal solution that makes a contact with the internal electrode and a liquid junction that continues into the internal solution, wherein
    the liquid junction includes a gel of hydrophobic ionic liquid including a hydrophobic salt with a melting point less than or equal to 100° Celsius and whose solubility in water is less than or equal to several m mol $dm^{-3}$.

2. The reference electrode described in claim 1, wherein the hydrophobic ionic liquid is gelled by a high polymer compound.

3. The reference electrode described in claim 2, wherein the high polymer compound is at least one kind of a compound selected from a group consisting of vinylidene fluoride-hexafluoropropylene copolymer, polymethylmethacrylate, polyacrylonitrile, polybutylacrylate, and other synthetic rubber.

4. The reference electrode described in claim 1, wherein the hydrophobic ionic liquid comprises a cation and an anion;
    the cation is at least more than or equal to one of quaternary ammonium cation, quaternary phosphonium cation, or quaternary arsonium cation, and
    the anion is at least more than or equal to one of $[R_1SO_2NSO_2R_2]^-$ (each of $R_1$, $R_2$ is perfluoroalkyl group of carbon number 1 through 5 respectively), borate ion containing fluorine and tetravalent boron, bis (2-ethylhexyl) sulfosuccinate, $AlCl_4^-$, $Al_3Cl_7^-$, $NO_3^-$, $BF_4^-$, $PF_6^-$, $CH_3COO^-$, $CF_3COO^-$, $CF_3SO_3^-$, $(CF_3SO_2)_2N^-$, $AsF_6^-$, $SbF_6^-$, $F(HF)_n^-$, $CF_3CF_2CF_2SO_3^-$, $(CF_3CF_2SO_2)_2N^-$, or $CF_3CF_2CF_2COO^-$.

5. The reference electrode described in claim 4, wherein the cation is at least more than or equal to one of a chemical formula

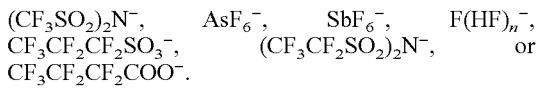

where $R_3$ expresses an alkyl group of a carbon number 1 through 12 and the alkyl group may include a heteroatom, a chemical formula

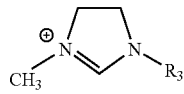

where $R_4$ expresses an alkyl group of a carbon number 12 through 18 and the alkyl group may include a heteroatom, a chemical formula

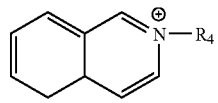

where $R_5$ expresses an alkyl group of a carbon number 12 through 18 and the alkyl group may include a heteroatom, a chemical formula

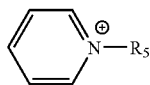

where $R_6$, $R_7$ express hydrogen or an alkyl group of a carbon number 1 through 12 and the alkyl group may include a heteroatom, or a chemical formula

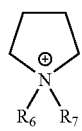

where $R_8$, $R_9$, $R_{10}$, $R_{11}$ express a alkyl group, a phenyl group of a carbon number 1 through 12, and the alkyl group may include a heteroatom.

6. The reference electrode described in claim 4, wherein the cation is at least more than or equal to one of 1-alkyl-3-metylimidazolium ion (a carbon number of the alkyl group is 4, 6, 8, 10 or 12), N-alkyl isoquinolinium (a carbon number of the alkyl group is 12, 14, 16 or 18), or N-alkyl pyridinium (a carbon number of the alkyl group is 12, 14, 16 or 18).

7. The reference electrode described in claim 4, wherein the borate ion is at least more than or equal to one of a fluoroborate ion, a tetrakis (3, 5-bis (trifluoromethyl) phenyl) borate ion, or a perfluoroalkyl trifluoro borate ion (a carbon number of the alkyl group is 1 through 5).

8. The reference electrode described in claim 1, wherein the internal solution is gelled.

9. A composite electrode characterized by comprising the reference electrode described in claim 1 and an ion selective electrode.

10. A salt bridge characterized by comprising:

a gelled hydrophobic ionic liquid including a hydrophobic slat with a melting point less than or equal to 100° Celsius and whose solubililty in water is less than or equal to several m mol $dm^{-3}$.

11. The salt bridge described in claim 10, wherein the hydrophobic ionic liquid is gelled by a high polymer compound.

12. The salt bridge described in claim 11, wherein the high polymer compound is at least one kind of a compound selected from a group consisting of vinylidene fluoride-hexafluoropropylene copolymer, polymethylmethacrylate, polyacrylonitrile, polybutylacrylate, and other synthetic rubber.

13. The salt bridge described in claim 10, wherein the hydrophobic ionic liquid comprises a cation and an anion;

the cation is at least more than or equal to one of quaternary ammonium cation, quaternary phosphonium cation, or quatemary arsonium cation, and the anion is at least more than or equal to one of $[R_1SO_2NSO_2R_2]^-$ (each of $R_1$, $R_2$ is perfluoroalkyl group of carbon number 1 through 5 respectively), borate ion containing fluorine and tetravalent boron, bis (2-ethylhexyl) sulfosuccinate, $AlCl_4^-$, $Al_3Cl_7^-$, $NO_3^-$, $BF_4^-$, $PF_6^-$, $CH_3COO^-$, $CF_3COO^-$, $CF_3SO_3^-$, $(CF_3SO_2)_2N^-$, $(CF_3SO_2)_3C^-$, $AsF_6^-$, $SbF_6^-$, $F(HF)_n^-$, $CF_3CF_2CF_2SO_3^-$, $(CF_3CF_2SO_2)_2N^-$, or $CF_3CF_2CF_2COO^-$.

14. The salt bridge described in claim 13, wherein the cation is at least more than or equal to one of a chemical formula

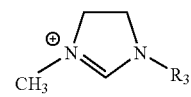

where $R_3$ expresses an alkyl group of a carbon number 1 through 12 and the alkyl group may include a heteroatom, a chemical formula

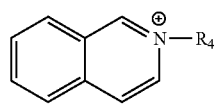

where $R_4$ expresses an alkyl group of a carbon number 12 through 18 and the alkyl group may include a heteroatom, a chemical formula

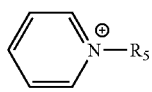

where $R_5$ expresses an alkyl group of a carbon number 12 through 18 and the alkyl group may include a heteroatom, a chemical formula

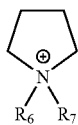

where $R_6$, $R_7$ express hydrogen or an alkyl group of a carbon number 1 through 12 and the alkyl group may include a heteroatom, or a chemical formula

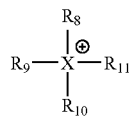

where $R_8$, $R_9$, $R_{10}$, $R_{11}$ express an alkyl group, a phenyl group or a benzyl group of a carbon number 1 through 12, and the alkyl group may include a heteroatom.

15. The salt bridge described in claim 13, wherein
the cation is at least more than or equal to one of 1-alkyl-3-metylimidazolium ion (a carbon number of the alkyl group is 4, 6, 8, 10 or 12), N-alkyl isoquinolinium (a carbon number of the alkyl group is 12, 14, 16 or 18), or N-alkyl pyridinium (a carbon number of the alkyl group is 12, 14, 16 or 18).

16. The salt bridge described in claim 13, wherein the borate ion is at least more than or equal to one of a fluoroborate ion, a tetrakis (3, 5-bis (trifluoromethyl) phenyl) borate ion, or a perfluoroalkyl trifluoro borate ion (a carbon number of the alkyl group is 1 through 5).

17. A reference electrode comprising:
an internal electrode and a liquid junction that is in contact with an internal solution that immerses the internal electrode, wherein
the liquid junction is formed by a gelled hydrophobic ionic liquid formed in a form of a membrane including a hydrophobic salt with a melting point less than or equal to 100° Celsius and whose solubility in water is less than or equal to several m mol dm$^{-3}$.

18. The reference electrode described in claim 17, and comprising a support tube to accommodate the internal electrode and the internal solution and a membrane fixing part to fix the gelled ionic liquid membrane to a distal end face of the support tube, wherein
the gelled ionic liquid membrane is fixed by the membrane fixing part through an elastic body lying between the distal end face of the support tube and the gelled ionic liquid membrane.

19. The reference electrode described in claim 18, wherein the elastic body is an O-ring.

20. An ionic concentration measuring device comprising:
an electrode for measurement,
a reference electrode; and
an operational unit that calculates a concentration of an ion to be an object to measure in a sample solution based on a difference in potential generated at a time when the electrode for measurement and the reference electrode are immersed in the sample solution, wherein
a liquid junction of the reference electrode is made by the use of a gelled hydrophobic ionic liquid including a hydrophobic salt with a melting point less than or equal to 100° Celsius and whose solubility in water is less than or equal to several m mol dm$^{-3}$.

* * * * *

UNITED STATES PATENT AND TRADEMARK OFFICE
CERTIFICATE OF CORRECTION

PATENT NO. : 7,628,901 B2
APPLICATION NO. : 11/432973
DATED : December 8, 2009
INVENTOR(S) : Kakiuchi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 861 days.

Signed and Sealed this

Second Day of November, 2010

David J. Kappos
*Director of the United States Patent and Trademark Office*